United States Patent [19]

Guzzi et al.

[11] 4,313,950
[45] Feb. 2, 1982

[54] ANTIREPRODUCTIVE TRICYCLIC ORTHO-FUSED NITROGEN CONTAINING COMPOUNDS

[75] Inventors: Umberto Guzzi, Milan; Amedeo Omodei-Sale, Voghera; Giulio Galliani, Monza, all of Italy

[73] Assignee: Gruppo Lepetit S.p.A., Milan, Italy

[21] Appl. No.: 230,138

[22] Filed: Jan. 30, 1981

Related U.S. Application Data

[62] Division of Ser. No. 87,371, Oct. 23, 1979, Pat. No. 4,275,066.

[51] Int. Cl.³ .................... A61K 31/47; C07D 471/04
[52] U.S. Cl. ................................ 424/258; 260/245.6; 424/273 R; 546/84; 548/324
[58] Field of Search .................. 546/84; 548/324; 260/245.6; 424/273 R, 258

[56] References Cited

U.S. PATENT DOCUMENTS 4,075,342  2/1978  Sale et al. .................... 546/84 X
4,100,165  7/1978  Houlihan ....................... 546/84
4,113,731  9/1978  Winters et al. ............... 424/258 X Primary Examiner—Richard A. Schwartz

[57] ABSTRACT

New tricyclic ortho-fused nitrogen containing compounds of the following formula:

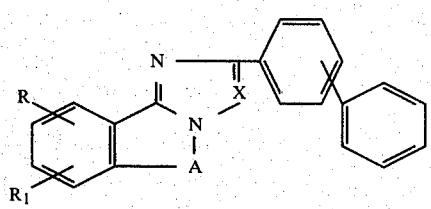

wherein R and $R_1$ are independently selected from hydrogen, fluoro, chloro, bromo and $(C_1-C_4)$alkoxy; A may be $-CH_2-$, $-CH_2-CH_2-$, $-CH=CH-$ or $-(CH_2)_3-$; X represents a nitrogen atom or the group CH; and salts therewith of pharmaceutically acceptable acids.

The compounds possess an outstanding antireproductive utility.

8 Claims, No Drawings

ANTIREPRODUCTIVE TRICYCLIC ORTHO-FUSED NITROGEN CONTAINING COMPOUNDS

This is a division of application Ser. No. 087,371, filed Oct. 23, 1979, now U.S. Pat. No. 4,275,066.

BACKGROUND OF THE INVENTION 1,2,4-Triazolo[5,1-a]isoindoles, 1,2,4-triazolo[5,1-a]isoquinolines and the corresponding 5,6-dihydro derivatives, all of them bearing a phenyl group at the 2-position, are known from U.S. Pat. Nos. 4,007,276 and 4,075,341. Imidazo[1,2-a]isoquinolines bearing a phenyl group at the 2-position are known from U.S. Pat. No. 4,075,342. The phenyl groups at the 2-position of the above mentioned heterocyclic structures may be also variously substituted (e.g. by alkoxy, allyloxy, halo, alkyl and so on). The biphenylyl substitution, however, has never been described.

SUMMARY OF THE INVENTION

The present invention relates to certain new tricyclic ortho-fused nitrogen containing compounds having anti-reproductive utility, to the processes for their manufacture and to their use as antireproductive agents. More particularly, the present invention relates to new tricyclic ortho-fused nitrogen containing compounds of the following formula:

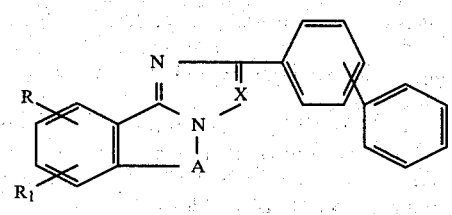

I wherein R and $R_1$ are independently selected from hydrogen, fluoro, chloro, bromo and $(C_{1-4})$alkoxy; A may be —$CH_2$—, —$CH_2$—$CH_2$—, —CH=CH— or —$(CH_2)_3$—; X represents a nitrogen atom or the group CH; and salts therewith of pharmaceutically acceptable acids.

When, in the formula I above, X represents the nitrogen atom, the following four structures may be identified:

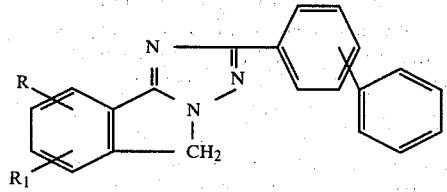

(a) 1,2,4-triazolo [5,1-a] isoindole

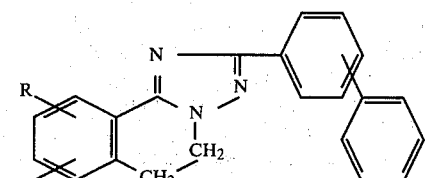

(b) 5,6-dihydro-1,2,4-triazolo [5,1-a] isoquinoline

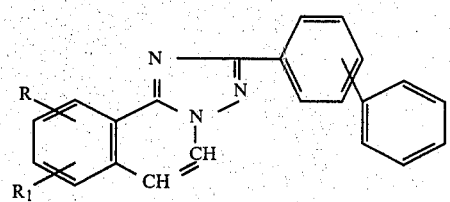

(c) 1,2,4-triazolo [5,1-a] isoquinoline

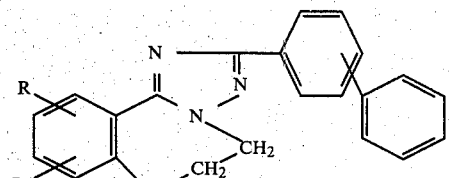

(d) 6,7-dihydro-5H-1,2,4-triazolo [5,1-a] [2] benzazepine

When, in the formula I above, X represents the group CH, the following four structures may be identified:

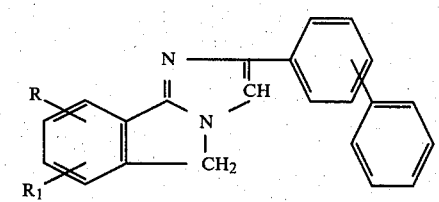

(e) imidazo [2,1-a] isoindole

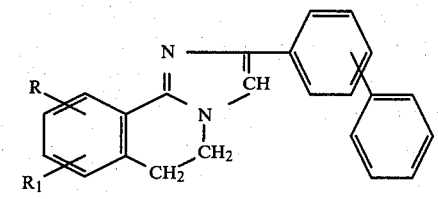

(f) 5,6-dihydro-imidazo [2,1-a] isoquinoline

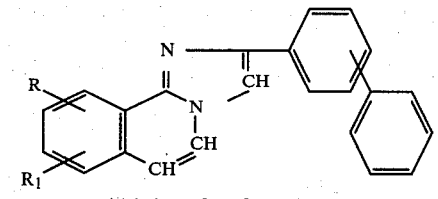

(g) imidazo [2,1-a] isoquinoline

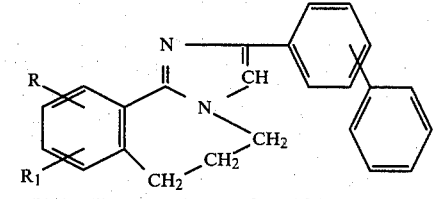

(h) 6,7-dihydro-5H-imidazo [2,1-a] [2] benzazepine

A preferred group of compounds comprises those compounds of formula I wherein A is —$CH_2$—$CH_2$— or —CH=CH—, X represents a nitrogen atom or the group CH and R and $R_1$ both represent hydrogen; and salts therewith of pharmaceutically acceptable acids.

A most preferred group of compounds comprises those compounds of formula I wherein A is —$CH_2$—$CH_2$— or —CH=CH—, X represents a nitrogen atom and R and $R_1$ both represent hydrogen; and salts therewith of pharmaceutically acceptable acids.

Another most preferred group of compounds comprises those compounds of formula I wherein A is —$CH_2$—$CH_2$— or —CH=CH—, X is the group CH and R and $R_1$ both represent hydrogen; and salts therewith of pharmaceutically acceptable acids. Pharmacologically-acceptable salts include those derived from mineral acids such as hydrochloric acid, hydrobromic acid, sulfuric acid as well as those derived from organic acids such as lactic, maleic, succinic, fumaric, oxalic, glutaric, citric, malic, tartaric, p-toluenesulfonic, benzenesulfonic, methanesulfonic, cyclohexanesulfonic acid and the like. They are prepared according to conventional methods.

The compounds of the invention can be prepared by different methods which essentially depend on the nature of the symbol X and the reacting substrates. As an example, the compounds (a) through (d) ie., those of formula I wherein X is the nitrogen atom, can be prepared following substantially the same procedure described in U.S. Pat. No. 4,075,341 by condensing a compound of formula:

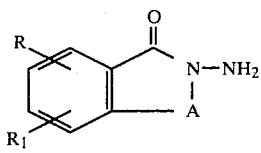

wherein R, $R_1$ and A are defined as above, with a biphenylyl derivative of formula

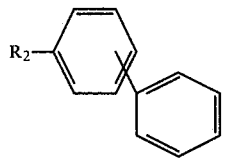

wherein $R_2$ represents one of the following groups:

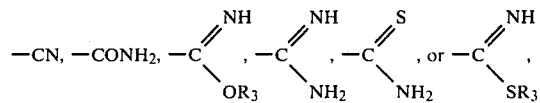

in which $R_3$ is an alkyl group from 1 to 3 carbon atoms. Both reactants may also be employed in the form of their corresponding acid salts.

However, according to one aspect of this invention, the condensation is carried out simply by contacting a molar proportion of the intermediate compound of formula II with at least one molar equivalent of the derivative of formula III for a period of time varying from about 5 to about 15 hours, optionally but not preferably in an organic solvent which may be selected from ($C_{1-4}$)alkanols, ($C_{1-4}$)alkoxy-($C_{1-4}$)alkanols, ethylene glycol, propylene glycol and mixtures thereof. The temperature at which the condensation takes place may vary from about 60° C. to the reflux temperature of the reaction mixture.

The desired end compounds are finally recovered and purified by means of techniques which are entirely familiar to a person skilled in the art. These techniques comprise removing the solvent by evaporation, cooling the reaction mixture until a precipitate crystallizes out, or extracting the final product by means of a suitable solvent which is subsequently evaporated. If necessary, the further purification is obtained by column chromatography or recrystallization.

A useful method for preparing compounds of formula I wherein X is the nitrogen atom and A is the group —CH=CH— comprises contacting a 2-amino-isoquinoline-1(2H)-one of formula

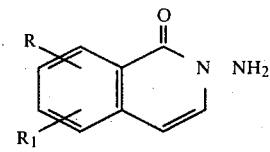

wherein R and $R_1$ are defined as above, with a nitrile of formula

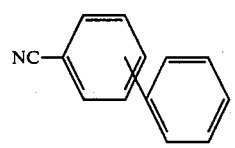

The reaction between compound IV and compound V can be carried out in a suitable solvent system but it can also be carried out in the absence of solvent by simply mixing the two reactants, preferably together with a catalyst. When the reaction is carried out in large batches, it is however desirable to add some solvent to lower the viscosity of the reaction mass and to facilitate the mixing of the reactants. A wide variety of solvents may be used.

Suitable solvents are for instances the alkanols such as methanol, ethanol, propanol and butanol, the lower alkoxy-alkanols such as methoxy-ethanol, ethoxy-ethanol and propoxy-ethanol, chlorinated-lower hydrocarbons, ethylene glycol, benzene, chlorobenzene, toluene, nitrobenzene, tetrahydrofuran, dioxane, dimethylformamide, dimethylsulfoxide, hexamethylphosphoric triamide and their mixture. The temperature of the reaction may range between the room temperature and the boiling temperature of the reaction mixture when it is carried out in a solvent. In general, temperatures between 60° and 160° C. are preferred since under these conditions the reaction rate is sufficiently rapid and the formation of undesired side product is prevented.

The two reactants are generally used in about equimolecular amounts, although in some cases an 1 to 20 percent molar excess of the nitrile may be added, in particular, to facilitate the mixing when the reaction is carried out in the absence of solvents. The reaction is generally carried out in the presence of a catalyst. Basic catalysts such as alkali metal hydroxides, alkoxides and hydrides were found to give satisfactory results. Tertiary organic amines may also be suitable employed as the catalyst, as well as transition metal salts and elemental sulfur. Among transition metal salts ferric chloride and zinc acetate are particularly preferred. The obtained end products are recovered by means of known procedures. The reactants of formula IV may be prepared through several methods.

The most convenient procedures involve as the final step the reaction between hydrazine and an isocoumarin of formula

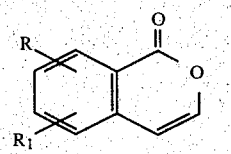

wherein R and R₁ have the same meanings as before. The preparation of the compounds VI is well documented in the literature and may be conveniently performed through bromination with Br₂ of the corresponding 1-isochromanone followed by dehydrobromination with triethylamine in 1,2-dichloroethane.

The reaction between hydrazine and the selected isocoumarin is carried out at room temperature by utilizing aqueous hydrazine hydrate in ethanol, as the solvent. Subsequent addition of acids to the reaction mixture allow the transformation of the intermediate 2-amino-3,4-dihydro-3-hydroxy-isoquinoline-1(2H)-ones into the desired 2-amino-isoquinoline-1(2H)-one.

According to another aspect of the invention, the compounds (e) through (h) above, i.e., those of formula I wherein X is the group CH, are conveniently prepared by reacting a biphenylyl-halomethyl ketone of formula

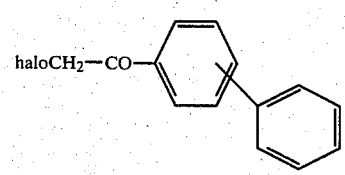

(halo = Cl, Br)

with a compound of formula

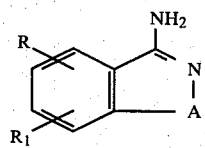

wherein A, R and R₁ are defined as above.

This reaction is carried out essentially according to the scheme outlined by F. Kröhnke et al, Chem. Ber., 95, 1128, 1962. In the actual practice, the reactants of formulas VII and VIII are contacted in about equimolecular proportions at a temperature comprised between the room temperature and the reflux temperature of the reaction mixture, preferably in the presence of an organic solvent such as, for instance, chlorinated ($C_{1-4}$) hydrocarbons, dioxane, tetrahydrofuran, benzene, toluene or mixtures thereof. The product which is obtained is the hydrohalide of the compound of formula I wherein X is the group CH and thus the corresponding free base is obtained by treatment with aqueous bases, such as diluted alkali hydroxides, carbonates or ammonium hydroxide. The recovery of the final products is achieved substantially by means of the methods illustrated for the recovery of the substances of structures (a) through (d).

It is finally to be noted that the compounds of formula I above wherein A is —CH₂—CH₂— can be prepared by catalytic hydrogenation with palladium on charcoal of the corresponding compounds where A is —CH=CH—. They, in turn, may be prepared by catalytically dehydrogenating the corresponding compounds wherein A is —CH₂—CH₂—. Among the several useful dehydrogenating agents which may be employed are sulfur, N-bromoacetamide, bromine, lead tetraacetate, chloranil and manganese dioxide. This latter may be prepared in a wet state, as described by Pratt et al, J. Org. Chem., 26, 2973, 1961 and is employed under the conditions reported by J. Goldman et al. in J. Org. Chem., 34, 1979, 1969.

The compounds of the present invention display a very interesting anti-reproductive utility. More particularly, they show a remarkable post-coital-post-implantation antifertility activity when administered, by different pharmacological routes, to laboratory animals, e.g. rats, hamsters, dogs, monkeys and baboons.

Moreover, the antifertility activity of these new compounds is not associated with other biological effects which are useful with hormonal substances.

The use of the novel tricyclic ortho-fused nitrogen containing compounds as antireproductive agents refers to all industrially applicable aspects and acts of said use, including the embodying of the novel compounds into pharmaceutical compositions. The pharmaceutical compositions containing said active compounds are in fact a further specific object of this invention.

Fertility regulation can usually be achieved in a number of ways through the administration of hormonal substances. These can involve ovulation inhibition, ova transport, fertilization, implantation of the zygote, resorption of the fetus or abortion. Only with ovulation inhibition has there developed a successful method that is clinically useful.

The compounds of this invention allow an entirely new approach to this problem in which a non-hormonal compound can be administered parenterally, orally or by intravaginal route once or more times as needed after a "missed period" or due to induce termination of a more advanced pregnancy.

Representative experiments for assessing antifertility activity were carried out with female Syrian golden hamsters weighing 100 to 130 g. The animals were mated and the presence of sperm in the vagina was taken as evidence of mating. The day sperm was detected was considered day one of pregnancy, since in our laboratories and those of other investigators 90 to 100% of animals that mate as evidenced by vaginal sperm are pregnant.

Pregnancy was later confirmed at the time of autopsy by presence of fetuses or implantation sites in the uterus. Even if an animal aborts the fetus, implantation scars still remain as evidence that the animal has been pregnant. The compounds of the invention, which possess a high solubility in the commonly employed pharmaceutical vehicles, were dissolved in sesame oil containing 20% of benzyl benzoate and administered subcutaneously in doses of 10 mg/kg daily for 5 days beginning on day 4 of pregnancy (days 4–8).

The animals were autopsied on day 14 of pregnancy and the uteri were examined for evidence of pregnancy (implantation sites, fetal resorptions or live fetuses), hemorrhage, and evidence of abnormalities of the uterus, placenta or fetuses. A compound was considered to be active if there was a reduction of live fetuses in at least 60% of the treated animals and the presence of implantation sites proves the animal to have been pregnant. The compounds of the invention proved to be active according to the above mentioned criteria.

The compounds were then studied for dose-activity relationships and the corresponding $ED_{50}$ values i.e., 100% activity (absence of live fetuses) in 50% of the animals, were also determined. The following Table reports the $ED_{50}$ values of some representative compounds of the invention:

TABLE I

| Compound of Example | $ED_{50}$ mg/kg s.c. hamsters |
|---|---|
| 1 | 0.015 |
| 3 | 0.05 |
| 4 | 0.7 |
| 6 | 0.02 |

The same criteria and experimental conditions as above were also applied when the anti-reproductive activity of the compounds of the invention was investigated in other animal species such as, for instance, rats, dogs, monkeys and baboons.

In representative experiments, female Sprague-Dawley rats weighing from 200 to 300 g. were treated subcutaneously with a dosage of 20 mg/kg of the compound to be tested, dissolved in sesame oil containing 20% of benzyl benzoate, for five consecutive days starting from day 6 of pregnancy. The rats were killed and autopsied on day 16 and the uteri were examined as seen above for hamsters.

Also in this experiment the compounds of the invention caused a reduction of live fetuses in at least 60% of the treated rats. The $ED_{50}$ value of the compound of Example 1 was determined and is reported in the following Table:

TABLE II

| Compound of Example | $ED_{50}$ mg/kg s.c. rats |
|---|---|
| 1 | 0.55 |

Favorable results were also obtained by administering the compounds of the invention by oral route. The experiments for assessing this property were carried out on hamsters following the same procedures as above, with the obvious exception that the compounds were administered orally instead of subcutaneously.

The reduction of about 60% of live fetuses was observed at an oral dosage of 10 mg/kg.

The $ED_{50}$ values of the compounds of Examples 1, 3 and 6 were also determined and are reported in the following Table:

TABLE III

| Compound of Example | $ED_{50}$ mg/kg p.o. hamsters |
|---|---|
| 1 | 0.20 |
| 3 | 0.50 |
| 6 | 0.30 |

The compound of the invention proved to be active also when administered by intravaginal route. In a representative experiment on hamsters, the compound of Example 1 displayed an $ED_{50}$ of about 0.20 mg/kg.

Finally, the compounds of the invention display a very low toxicity. In fact, their $LD_{50}$-values, determined according to Lichtfield and Wilcoxon, Journ. Pharm. Expt. Ther., 96, 99, 1949, are never lower than 600 mg/kg when administered to mice by intraperitoneal route.

The facts that the compounds of the invention possess an outstanding antireproductive activity even when administered by oral route and are very soluble in the common pharmaceutical carriers represent undoubtedly further important properties. As an example, the high solubility causes the compounds to be readily absorbable and incorporable into suitable and more tolerable injectable dosage forms which possess less drawbacks than corresponding forms wherein the active ingredient is suspended in the carrier. On the other hand, also the activity by oral or intravaginal route allows the compounds to be embodied into more acceptable pharmaceutical preparations.

It results, therefore, that the compounds of the invention may be administered by various routes: orally, subcutaneously, intramuscularly or intravaginally.

For oral administration the substances are compounded in such forms as tablets, dispersible powders, capsules, granules, syrups, elixirs and solutions.

The compositions for oral use may contain one or more conventional adjuvants, such as, for instance, sweetening agents, flavoring agents, coloring agents, coating and preservative agents, in order to provide an elegant and palatable preparation.

Tablets may contain the active ingredient admixed with conventional, pharmaceutically acceptable excipients, e.g. inert diluents, such as calcium carbonate, sodium carbonate, lactose and talc, granulating and disintegrating agents, such as, for instance, starch, alginic acid and sodium carboxymethylcellulose, binding agents, e.g. starch, gelating, gum-arabic and polyvinylpyrrolidone and lubricating agents, e.g. magnesium stearate, stearic acid and talc.

Syrups, elixirs and solutions are formulated as known in the art. Together with the active compound they may contain suspending agents, such as, for instance, methylcellulose, hydroxyethylcellulose, tragacanth and sodium alginate, wetting agents, e.g. lecithin, polyoxyethylene stearates and polyoxyethylene sorbitan monooleate, and the common preservative, sweetening and buffering agents.

A capsules or a tablet may contain the active ingredient alone or admixed with an inert solid diluent, such as, for instance, calcium carbonate, calcium phosphate and kaolin.

Besides the oral route, other useful ways for administering the compounds of the invention may be suitably employed, such as, for instance, the subcutaneous or the intramuscular administration.

The active ingredient is thus embodied into injectable dosage forms. Such compositions are formulated according to the art and may contain appropriate dispersing or wetting agents and suspending or buffering agents identical or similar to those mentioned above.

Sesame oil, benzyl alcohol, benzyl benzoate, peanut oil and their mixtures may also be suitably employed as vehicles. A vaginal insert may also contain the active ingredient in admixture with the common carriers, e.g. gelatin, adipic acid, sodium bicarbonate, lactose and analogs. The compounds of the invention may also be administered in the form of their nontoxic, pharmaceutically acceptable acid addition salts. Such salts possess the same degree of activity as the free bases, from which they are readily prepared by reacting the base with an appropriate acid and, accordingly, are included within the scope of the invention. Representative of such salts are the mineral acid salts, such as, for instance, the hydrochloride, hydrobromide, sulfate and the like, and the organic acid salts, such as the succinate, benzoate, acetate, p-toluenesulfonate, benzene sulfonate, maleate, tartrate, methanesulfonate, cyclohexylsulfonate and the like.

The dosage of active ingredient employed for inhibiting reproduction may vary within wide limits, depending on the nature of the compound.

Generally, good results are obtained when the compounds of the above formula I are administered in a single dosage from 0.1 to 25 mg/kg intramuscularly or in a multiple dosage (for from 5 to 10 days) of 0.5 to 25 mg/kg orally or intravaginally.

The dosage forms useful for this purpose generally contain from about 10 to about 600 mg of the active ingredient in admixture with a solid or liquid pharmaceutically acceptable carrier or diluent.

The following examples illustrate the process of the invention and described in detail somo compounds of the general formula I without limiting the scope of the invention.

EXAMPLE 1

2-[(1,1'-Biphenyl)-4-yl]-1,2,4-triazolo[5,1-a]isoquinoline

A solution prepared from 0.075 g. of sodium dissolved in 20 ml of absolute ethanol was added to a suspension of 0.640 g. (0.004 mole) of 2-amino-isoquinoline-1(2H)-one and 0.720 g. (0.004 mole) of 4-phenyl-benzonitrile in 20 ml of absolute ethanol. The resulting mixture was refluxed for 30 minutes on an oil bath, then 15 ml. of ethylene glycol were added and the ethanol was distilled off by adjusting the temperature of the oil bath at about 150° C. After three hours the reaction mixture was cooled to room temperature whereby the title compound crystallized out. It was recovered by filtration and re-crystallized from a mixture of methylene chloride/diethyl ether=1/1. Yield 650 mg. M.p. 203°-5° C.

EXAMPLE 2

2-[(1,1'-Biphenyl)-3-yl]-1,2,4-triazolo[5,1-a]isoquinoline

This compound was prepared according to the procedure of the foregoing Example, starting from 2-amino-isoquinoline-1(2H)-one and 3-phenyl-benzonitrile. Yield 49%. M.p. 167°-69° C. (from ethyl acetate).

EXAMPLE 3

2-[(1,1'-Biphenyl)-4-yl]-5,6-dihydro-1,2,4-triazolo[5,1-a]isoquinoline

A mixture consisting of 1.94 g. (0.0086 mole) of 4-phenyl-benzimidic acid ethyl ester and 0.972 g. (0.006 mole) of 2-amino-3,4-dihydro-isoquinoline-2(1H)-one was heated on an oil bath at a temperature of 90° C. for 5 hours. The temperature of the bath was subsequently raised to 200° C. and kept as such overnight. Upon cooling, the obtained mass was dissolved in methylene chloride and chromatographed through silicagel by using as the eluting systems firstly light petroleum/diethyl ether=9/1 and then light petroleum/diethyl ether=8/2 (volume/volume). The fractions containing the title product were collected and the resulting solution was concentrated to small volume. The title product crystallized out and was recovered by filtration. Yield 1.180 g. M.p. 143°-44° C. (from diethyl ether/hexane).

EXAMPLE 4

2-[(1,1'-Biphenyl-4-yl]-5H-1,2,4-triazolo[5,1-a]isoindole

This compound was prepared according to the procedure of Example 3, starting from N-aminophthalimidine and 4-phenyl-benzimidic acid ethyl ester. Yield 52%. M.p. 231° C. (from ethyl acetate).

EXAMPLE 5

2-[(1,1'-Biphenyl)-4-yl]-6,7-dihydro-5H-1,2,4-triazolo[5,1-a][2]benzazepine

This compound was prepared according to the procedure of Example 3 starting from 2-amino-4,5-dihydro-2-benzazepine-1(2H,3H)-one and 4-phenyl-benzimidic acid ethyl ester. Yield 63%. M.p. 135°-37° C. (from diethyl ether).

EXAMPLE 6

2-[(1,1'-Biphenyl)-4-yl]-imidazo[2,1-a]isoquinoline

A solution of 4.32 g. (0.03 mole) of 1-amino-isoquinoline and 8.25 g. (0.03 mole) of [(1,1'-biphenyl)-4-yl]-bromomethyl-ketone in 100 ml. of chloroform was heated on a boiling water bath for about 10 minutes until a precipitate separated. The solvent was distilled off at atmospheric pressure and the residue was heated under vacuum for 30 minutes at 100° C. It was subsequently taken up with 50 ml of water and the resulting solution was made alkaline by means of 70 ml. of aqueous 10% sodium hydroxide. After extracting with 500 ml. of methylene chloride and evaporating the solvent, a residue was obtained which was re-crystallized from ethylene glycol monomethylether. Yield 3.0 g. M.p. 221°-22° C.

EXAMPLE 7

A sugar coated table is prepared from

| | |
|---|---|
| 2-[(1,1'-Biphenyl)-4-yl]-1,2,4-triazolo-[5,1-a]isoquinoline | 50 mg |
| Sodium carboxymethylcellulose | 5 mg |
| Magnesium stearate | 5 mg |
| Gelatin | 5 mg |
| Starch | 5 mg |
| Saccharose | 27 mg |
| gum arabic, lactose, titan dioxane, aluminum lac according to conventional procedures | |

Example 8

A vial for injectable use is prepared from

| | |
|---|---|
| 2[(1,1'-Biphenyl)-4-yl]-1,2,4-triazolo[5,1-a]isoquinoline | 30 mg |
| Benzyl benzoate | 220 mg |
| Sesame oil q.s. to | 2 ml |

EXAMPLE 9

A tablet is prepared from

| | |
|---|---|
| 2-[(1,1'-Biphenyl)-4-yl]-imidazo[2,1-a]isoquinoline | 100 mg |
| Levilite | 80 mg |
| Starch | 80 mg |
| Magnesium stearate | 10 mg |

The following compounds may be prepared according to the procedure outlined in the foregoing Examples:

2-[(1,1'-Biphenyl)-3-yl]-5H-1,2,4-triazolo[5,1-a]isoindole
2-[(1,1'-Biphenyl)-4-yl]-7-chloro-5H-1,2,4-triazolo[5,1-a]isoindole
2-[(1,1'-Biphenyl)-4-yl]-8-chloro-5H-1,2,4-triazolo[5,1-a]isoindole
2-[(1,1'-Biphenyl)-4-yl]-8-methoxy-5H-1,2,4-triazolo[5,1-a]isoindole
2-[(1,1'-Biphenyl)-4-yl]-7,8-dichloro-5H-1,2,4-triazolo[5,1-a]isoindole
2-[(1,1'-Biphenyl)-2-yl]-5H-1,2,4-triazolo[5,1-a]isoindole
2-[(1,1'-Biphenyl)-3-yl]-5,6-dihydro-1,2,4-triazolo[5,1-a]isoquinoline
2-[(1,1'-Biphenyl)-2-yl]-5,6-dihydro-1,2,4-triazolo[5,1-a]isoquinoline
2-[(1,1'-Biphenyl)-4-yl]-7-chloro-5,6-dihydro-1,2,4-triazolo[5,1-a]isoquinoline
2-[(1,1'-Biphenyl)-4-yl]-8-chloro-5,6-dihydro-1,2,4-triazolo[5,1-a]isoquinoline
2-[(1,1'-Biphenyl)-4-yl]-8,9-dichloro-5,6-dihydro-1,2,4-triazolo[5,1-a]isoquinoline
2-[(1,1'-Biphenyl)-4-yl]-7-methoxy-5,6-dihydro-1,2,4-triazolo[5,1-a]isoquinoline
2-[(1,1'-Biphenyl)-4-yl]-9-methoxy-5,6-dihydro-1,2,4-triazolo[5,1-a]isoquinoline
2-[(1,1'-Biphenyl)-4-yl]-8,9-dimethoxy-5,6-dihydro-1,2,4-triazolo[5,1-a]isoquinoline
2-[(1,1'-Biphenyl)-4-yl]-7-ethoxy-5,6-dihydro-1,2,4-triazolo[5,1-a]isoquinoline
2-[(1,1'-Biphenyl)-4-yl]-9-ethoxy-5,6-dihydro-1,2,4-triazolo[5,1-a]isoquinoline
2-[(1,1'-Biphenyl)-2-yl]-1,2,4-triazolo[5,1-a]isoquinoline
2-[(1,1'-Biphenyl)-4-yl]-9-chloro-1,2,4-triazolo[5,1-a]isoquinoline
2-[(1,1'-Biphenyl)-4-yl]-8-chloro-1,2,4-triazolo[5,1-a]isoquinoline
2-[(1,1'-Biphenyl)-4-yl]-8,9-dichloro-1,2,4-triazolo[5,1-a]isoquinoline
2-[(1,1'-Biphenyl)-4-yl]-7-methoxy-1,2,4-triazolo[5,1-a]isoquinoline
2-[(1,1'-Biphenyl)-4-yl]-9-methoxy-1,2,4-triazolo[5,1-a]isoquinoline
2-[(1,1'-Biphenyl)-4-yl]-8,9-dimethoxy-1,2,4-triazolo[5,1-a]isoquinoline
2-[(1,1'-Biphenyl)-4-yl]-7-ethoxy-1,2,4-triazolo[5,1-a]isoquinoline
2-[(1,1'-Biphenyl)-4-yl]-9-ethoxy-1,2,4-triazolo[5,1-a]isoquinoline
2-[(1,1'-Biphenyl)-3-yl]-6,7-dihydro-5H-1,2,4-triazolo[5,1-a][2]benzazepine
2-[(1,1'-Biphenyl-2-yl]-6,7-dihydro-5H-1,2,4-triazolo[5,1-a][2]benzazepine
2-[(1,1'-Biphenyl)-2-yl]-imidazo[2,1-a]isoindole
2-[(1,1'-Biphenyl)-3-yl]-imidazo[2,1-a]isoindole
2-[(1,1'-Biphenyl)-4-yl]-imidazo[2,1-a]isoindole
2-[(1,1'-Biphenyl)-4-yl]-7-chloro-imidazo[2,1-a]isoindole
2-[(1,1'-Biphenyl)-4-yl]-8-chloro-imidazo[2-1-a]isoindole
2-[(1,1'-Biphenyl)-4-yl]-8-methoxy-imidazo[2,1-a]isoindole
2-[(1,1'-Biphenyl)-2-yl]-5,6-dihydro-imidazo[2,1-a]isoquinoline
2-[(1,1'-Biphenyl)-3-yl]-5,6-dihydro-imidazo[2,1-a]isoquinoline
2-[(1,1'-Biphenyl)-4-yl]-5,6-dihydro-imidazo[2,1-a]isoquinoline
2-[(1,1'-Biphenyl)-4-yl]-9-chloro-5,6-dihydro-imidazo[2,1-a]isoquinoline
2-[(1,1'-Biphenyl)-4-yl]-8-chloro-5,6-dihydro-imidazo[2,1-a]isoquinoline
2-[(1,1'-Biphenyl)-4-yl]-8,9-dichloro-5,6-dihydro-imidazo[2,1-a]isoquinoline
2-[(1,1'-Biphenyl)-4-yl]-9-methoxy-5,6-dihydro-imidazo[2,1-a]isoquinoline
2-[(1,1'-Biphenyl)-4-yl]-8-methoxy-5,6-dihydro-imidazo[2,1-a]isoquinoline
2-[(1,1'-Biphenyl)-4-yl]-8,9-dimethoxy-5,6-dihydro-imidazo[2,1-a]isoquinoline
2-[(1,1'-Biphenyl)-2-yl]-imidazo[2,1-a]isoquinoline
2-[(1,1'-Biphenyl)-3-yl]-imidazo[2,1-a]isoquinoline
2-[(1,1'-Biphenyl)-4-yl]-7-chloro-imidazo[2,1-a]isoquinoline
2-[(1,1'-Biphenyl)-4-yl]-8-chloro-imidazo[2,1-a]isoquinoline
2-[(1,1'-Biphenyl)-4-yl)-7,8-dichloro-imidazo[2,1-a]isoquinoline
2-[(1,1'-Biphenyl-4-yl]-7-methoxy-imidazo[2,1-a]isoquinoline
2-[(1,1'-Biphenyl-4-yl]-8-methoxy-imidazo[2,1-a]isoquinoline
2-[(1,1'-Biphenyl)-4-yl]-7,8-dimethoxy-imidazo[2,1-a]isoquinoline
2-(1,1'-Biphenyl)-4-yl]-7-ethoxy-imidazo[2,1-a]isoquinoline
2-[(1,1'-Biphenyl)-4-yl]-8-ethoxy-imidazo[2,1-a]isoquinoline
2-[(1,1'-Biphenyl)-2-yl)]-6,7-dihydro-5H-imidazo[2,1-a][2]-benzazepine
2-[(1,1'-Biphenyl)-3-yl]-6,7-dihydro-5H-imidazo[2,1-a][2]-benzazepine
2-[(1,1'-Biphenyl)-4-yl]-6,7-dihydro-5H-imidazo[2,1-a][2]benzazepine

PREPARATION OF THE STARTING MATERIALS

(A) 2-Amino-isoquinoline-1(2H)-one

A solution of isocoumarin (26 g, 0.16 mol) in 95% ethanol (2000 ml) was treated with 25% hydrazine hydrate in water (64 ml, 0.32 mol) and stirred at room temperature for one hour. The precipitate of 2-amino-3,4-dihydro-3-hydroxy-1H(2H)-isoquinolinone was dissolved and dehydrated by addition of 10% hydrochloric acid (150 ml) at room temperature. After three hours, the mixture was neutralized with sodium carbonate and the ethanol recovered by distillation in vacuo. The title compound was isolated by filtration and extraction with chloroform to give 27.92 g (98%) of the product of the title, M.p. 103°–4° C.

(B) 2-Amino-4,5-dihydro-2-benzazepine-1(2H,3H)-one

A solution of 2.7 g of O-amino-sulfonic acid and 1.25 g of a 55% oily suspension of sodium hydride in 30 ml of dimethylformamide and 30 ml of tetrahydrofuran was gradually added at a temperature of 10° C. to a suspension of 9.66 g (0.0176 mol) 4,5-dihydro-2-benzazepine-1(2H,3H)-one. After standing for 1 hour at room temperature the mixture was poured into a saturated aqueous solution of NaCl, then the organic layer was separated and the mother liquors were extracted with 300 ml (3×100 ml) of an 1:1 (v:v) mixture of tetrahydrofuran and dimethylformamide. The organic phases were combined and brought to dryness. The obtained residue was subsequently taken up with 500 ml of ethyl acetate and the resulting organic solution was extracted with 200 ml (5×40 ml) of a 3% aqueous solution of HCl. The acidic extract was made alkaline with 5% aqueous sodium hydroxide and subsequently extracted with ethyl acetate. After evaporating the solvent, an oily residue was obtained which was distilled under reduced pressure. Yield: 10 g. of the title compound. B.p. 120° C./0.2 mmHg (C) 2-Amino-3,4-dihydro-isoquinoline-2(1H)-one The preparation of this compound is described in Belgian Pat. No. 780,885.

(D) N-Aminophthalimidine

The preparation of this compound is described by Bellasio et al., Annali di Chimica, 59, 451, 1969.

(E) 1-Amino-isoquinoline

This is a commercial product.

We claim:

1. A tricyclic orthofused nitrogen containing compound of formula

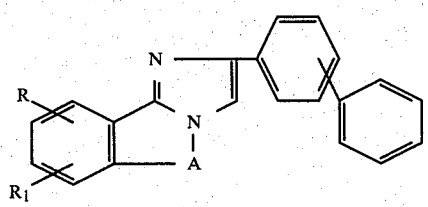

wherein R and $R_1$ are independently selected from hydrogen, fluoro, chloro, bromo and $(C_{1-4})$alkoxy; A may be —$CH_2$—, —$CH_2$—$CH_2$—, —CH=CH— or —$(CH_2)_3$—; or a salt therewith of a pharmaceutically-acceptable acid.

2. A compound as in claim 1 wherein A is —$CH_2$—$CH_2$— or —CH=CH— and R and $R_1$ both represent hydrogen; or a salt therewith of a pharmaceutically-acceptable acid.

3. An antireproductive pharmaceutical composition containing an effective antireproductive amount of a compound of formula

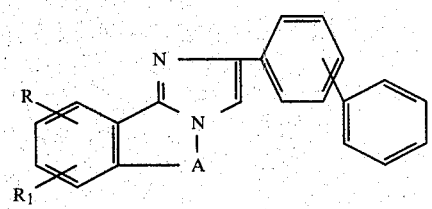

wherein A, R and $R_1$ are defined as in claim 1, in admixture with acceptable pharmaceutical carriers.

4. An antireproductive pharmaceutical composition containing from about 10 to about 600 mg. of a compound of formula

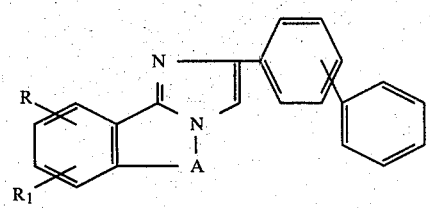

wherein A, R, and $R_1$ are defined as in claim 1, in admixture with acceptable pharmaceutical carriers.

5. A method for preventing reproduction in warm-blooded animals, which comprises administering to the animal a dosage varying from about 0.1 to about 25 mg/kg of body weight of a compound of formula

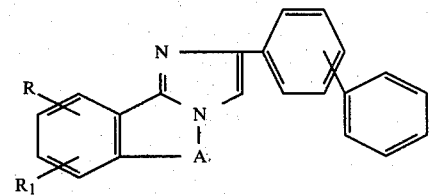

wherein A, R, and $R_1$ are defined as in claim 1.

6. The method of claim 5 wherein the compound is administered intramuscularly in a dosage of from about 0.1 to about 25 mg/kg of body weight.

7. The method of claim 5 wherein the compound is administered orally in a dosage of from about 0.5 to about 25 mg/kg of body weight.

8. The method of claim 5 wherein the compound is administered intravaginally in a dosage of from about 0.5 to about 25 mg/kg of body weight.

* * * * *